United States Patent [19]

Mackintosh et al.

[11] Patent Number: 4,769,324
[45] Date of Patent: Sep. 6, 1988

[54] ETHANOL PRODUCTION

[75] Inventors: Theresa D. Mackintosh, Boksburg; Ana P. Quintela, Germiston, both of South Africa

[73] Assignee: Sentrachem Limited, Johannesburg, South Africa

[21] Appl. No.: 805,116

[22] Filed: Dec. 5, 1985

[30] Foreign Application Priority Data

Dec. 10, 1984 [ZA] South Africa ............... 84/9591

[51] Int. Cl.[4] .................. C12P 39/00; C12P 7/06; C12P 7/14
[52] U.S. Cl. ........................ 435/42; 435/161; 435/162; 435/911; 435/942
[58] Field of Search ............ 435/161, 162, 42, 911, 435/942

[56] References Cited

U.S. PATENT DOCUMENTS 1,472,344 10/1923 Vasseux .................... 435/161
4,490,469 12/1984 Kirby et al. .............. 435/161

OTHER PUBLICATIONS

Dhawale et al., *Biotechnology Letters*, vol. 5, No. 3, 185-190 (1983).

*Primary Examiner*—Charles F. Warren
*Assistant Examiner*—Elizabeth A. Hanley
*Attorney, Agent, or Firm*—Fitch, Even, Tabin & Flannery

[57] ABSTRACT

The invention is directed to the production of ethanol by the fermentation of molasses in the presence of the yeasts *S. cerevisiae* and *Schwanniomyces castellii* (R69), which is capable of growing and producing amylase in a molasses-containing meduim. The amylase converts starch and higher sugars in the unfermentable component of the medium to a hexose sugar which is converted to ethanol by *S. cerevisiae*.

2 Claims, No Drawings

ETHANOL PRODUCTION

BACKGROUND OF THE INVENTION

This invention relates to ethanol production.

Ethanol is presently produced in substantial quantities by fermenting molasses in the presence of a suitable yeast such as *Saccharomyces cerevisiae*. These yeasts are able to effect a conversion of hexose sugars in the molasses to ethanol. However, the yeasts are not capable of effecting conversion of the starch fraction and higher sugars in molasses to ethanol. The starch fraction and higher sugars which have a potential to be converted to ethanol are thus not utilised and report as waste products.

SUMMARY OF THE INVENTION

According to the present invention, there is provided a method of producing ethanol by the fermentation of molasses in the presence of a yeast capable of converting hexose sugars to ethanol, characterised in that the process is also carried out in the presence of the yeast, *Schwanniomyces castellii* (R69), which is capable of growing and producing amylase in a molasses-containing medium.

DETAILED DESCRIPTION OF THE INVENTION

The amylolytic or starch-degrading *S. castellii* and the mutant derived therefrom (R69) are described, for example, in the article "Starch Hydrolysis by Derepressed Mutants of *Schwanniomyces Castellii*" by M. R. Dhawale and W. M. Ingledew, Biotechnology Letters, Vol. 5 No. 3, 185–190 (1983). This yeast is known to be capable of producing the enzymes α-amylase and glucamylase in a starch-based medium such as wheat-starch or soluble starch. However, this reference does not describe nor suggest that this yeast is capable of producing the amylase enzymes in a molasses-containing medium. These mediums are entirely different to the starch mediums used by the authors of this paper.

In the process of the present invention the *S. castellii* mutant produces the enzymes α-amylase and glucamylase which converts starch and higher sugars in the unfermentable component of the molasses substrate to a hexose sugar thereby making it available for conversion to ethanol by *Saccharomyces cerevisiae*. Higher yields of ethanol are thus produced from a given quantity of molasses than is possible in prior art processes.

It is essential that the mutant (R69) be subjected to various known acclimatisation procedures to adapt the culture to growth and amylase production in the molasses-containing medium. The molasses-containing growth medium will typically have a fermentable sugar content of 4 to 10 percent by weight, typically 8 percent by weight. By way of example, acclimatisation can be achieved by exposing the mutant to a molasses medium containing a high fermentable sugar concentration, e.g. 8 to 10 percent by weight, after a period of time isolating the survivors, exposing the survivors again to a molasses medium containing a high concentration of fermentable sugar, and repeating this until a fully acclimatised strain is produced.

The *S. castellii* mutant may be subjected to a series of seed stages of increasing volume and sugar concentration to produce an inoculum suitable for use in the process of the invention. These seed stages have the effect of increasing the concentration of the mutant to a desired level.

The acclimatised *S. castellii* and a yeast suitable to convert hexose sugars in molasses to ethanol, e.g. *S. cerevisiae*, will be introduced into a suitable molasses-containing medium and allowed to act in the medium to produce ethanol. The medium will generally contain a starting concentration of 4 to 8 percent fermentable sugars, i.e. glucose, fructose and sucrose. Additional increments of molasses are fed at various intervals during the process. Higher sugars and starch in the medium will be converted to hexose sugars by the amylase which is produced by the acclimatised *S. castellii*. The fermentation temperature will generally be controlled to about 32° C.

An example of the invention will now be described.

The process involves growing a culture of *S. castellii* (R69) through a series of aerated laboratory molasses seed stages of increasing volume and sugar concentration, the final laboratory seed stage (2×9 l), providing the inoculum of acclimatised *S. castellii* for a plant stage—the prefermenter. At the same time, a parallel series of laboratory seed stages intended for buildup of *S. cerevisiae* is carried out and inoculated into the prefermenter with *S. castellii*.

After a period of growth in the prefermenter, the entire contents are transferred to the fermenter where fresh molasses mash is also supplied. During fermentation the amylases produced by *S. castellii* hydrolyse the small quantities of starch and higher sugars present in the medium thereby producing more fermentable sugar from the same quantity of molasses. This is subsequently fermented by *S. cerevisiae* together with the other hexose sugars normally present in molasses. Therefore, the presence of *S. castellii* together with *S. cerevisiae* results in increased levels of ethanol produced as a result of additional sugar being made available.

Although *S. castellii* does produce some ethanol itself, this is very much a secondary function. It appears that the *S. castellii* is inhibited fairly early on in the process as it is not as ethanol tolerant as *S. cerevisiae*. Therefore, it appears that following amylase production, the culture dies early on in the process, thus using negligible sugar for the production of biomass. However, the amylase produced by *S. castellii* is not sensitive to the presence of ethanol and therefore, continues hydrolysing starch and higher sugars throughout fermentation.

The process of the invention was carried out experimentally and the improvement in ethanol yield obtained when *S. castellii* is grown together with *S. cerevisiae* at the same concentration of starch sugar in batch fermentations of molasses is shown by the following results obtained:

|  | % m/v Ethanol |
|---|---|
| Mixed cultures (*S. cerevisiae* + *S. castellii*) | 6,395 |
| Mixed cultures (*S. cerevisiae* + *S. castellii*) | 6,410 |
| *S. cerevisiae* alone | 6,010 |
| *S. cerevisiae* alone | 5,981. |

In a plant production of ethanol from molasses, it was found that the yield of ethanol could be increased from 8,5% m/v to 8,65–8,70% m/v when using a combination of *S. cerevisiae* and *S. castellii* instead of *S. cerevisiae* alone.

We claim:

1. A method of producing ethanol by the fermentation of molasses in the presence of a yeast *S. cerevisiae* characterized in that the process is also carried out in the presence of molasses acclimitized yeast, *S. castelli*, which is capable of growing and producing amylase enzymes in a molasses-containing medium.

2. A method of claim 1 wherein the *S. castellii* (R69) is capable of growing and producing amylase in molasses medium containing 4 to 10 percent by weight fermentable sugar.

* * * * *